United States Patent [19]

Reynolds

[11] Patent Number: 5,709,666

[45] Date of Patent: Jan. 20, 1998

[54] SYRINGE

[76] Inventor: David L. Reynolds, 305 Knowlton Road, P.O. Box 600, (Knowlton) Lac Brome, Quebec, Canada, J0E 1V0

[21] Appl. No.: 338,843

[22] Filed: Nov. 14, 1994

Related U.S. Application Data

[63] Continuation-in-part of Ser. No. 791,399, Nov. 14, 1991, Pat. No. 5,364,369.

[51] Int. Cl.$^6$ ........................................................ A61M 5/00
[52] U.S. Cl. ............................... 604/191; 604/89; 604/232; 604/415
[58] Field of Search ........................ 604/82, 87, 88, 604/89, 91, 92, 191, 200, 201, 203–205, 411, 413–416, 905, 187, 232; 206/222; 215/247

[56] References Cited

U.S. PATENT DOCUMENTS

| | | | |
|---|---|---|---|
| 2,176,042 | 10/1939 | Pittenger | 604/92 X |
| 2,724,883 | 11/1955 | Lockhart | 604/88 |
| 3,080,866 | 3/1963 | Friedman | 604/88 |
| 3,511,239 | 5/1970 | Tuschhoff | 604/89 |
| 3,563,373 | 2/1971 | Paulson | 604/88 X |
| 3,621,843 | 11/1971 | Metten | 604/88 |
| 3,735,900 | 5/1973 | Goves | 604/82 X |
| 4,834,717 | 5/1989 | Haber et al. | 604/193 |
| 5,158,546 | 10/1992 | Haber et al. | 604/87 |
| 5,478,337 | 12/1995 | Okamoto et al. | 604/413 |

*Primary Examiner*—Michael Powell Buiz
*Assistant Examiner*—A. T. Nguyen
*Attorney, Agent, or Firm*—Ridout & Maybee

[57] ABSTRACT

A prefilled syringe system is provided for two component pharmaceuticals, which is a combination of a first subassembly consisting of a capped bottomless pharmaceutical vial containing a first component and closed at its bottom end by a piston which can be connected to a plunger and a second subassembly consisting of a shell containing a second component and closed by a further piston and located in telescopable relationship with the plunger, a cap which can be forced onto the cap of the bottomless vial, and a double ended needle or a functionally equivalent cannula assembly which is caused to pierce both pistons as the assemblies are connected by forcing the cap onto the bottomless vial, thus placing the vials in communication. The shell vial is pressed towards the bottomless vial to express its contents into the latter, and the plunger and shell vial are then removed so that the cap and needle are left connected to the bottomless vial and the plunger may be connected to the piston of the bottomless vial to convert it into a syringe. The shell vial may telescope either over or within the plunger. In the first case, the plunger acts to operate the piston of the shell vial during expression of its contents, whereas in the latter case a separate component is required for this purpose.

5 Claims, 4 Drawing Sheets

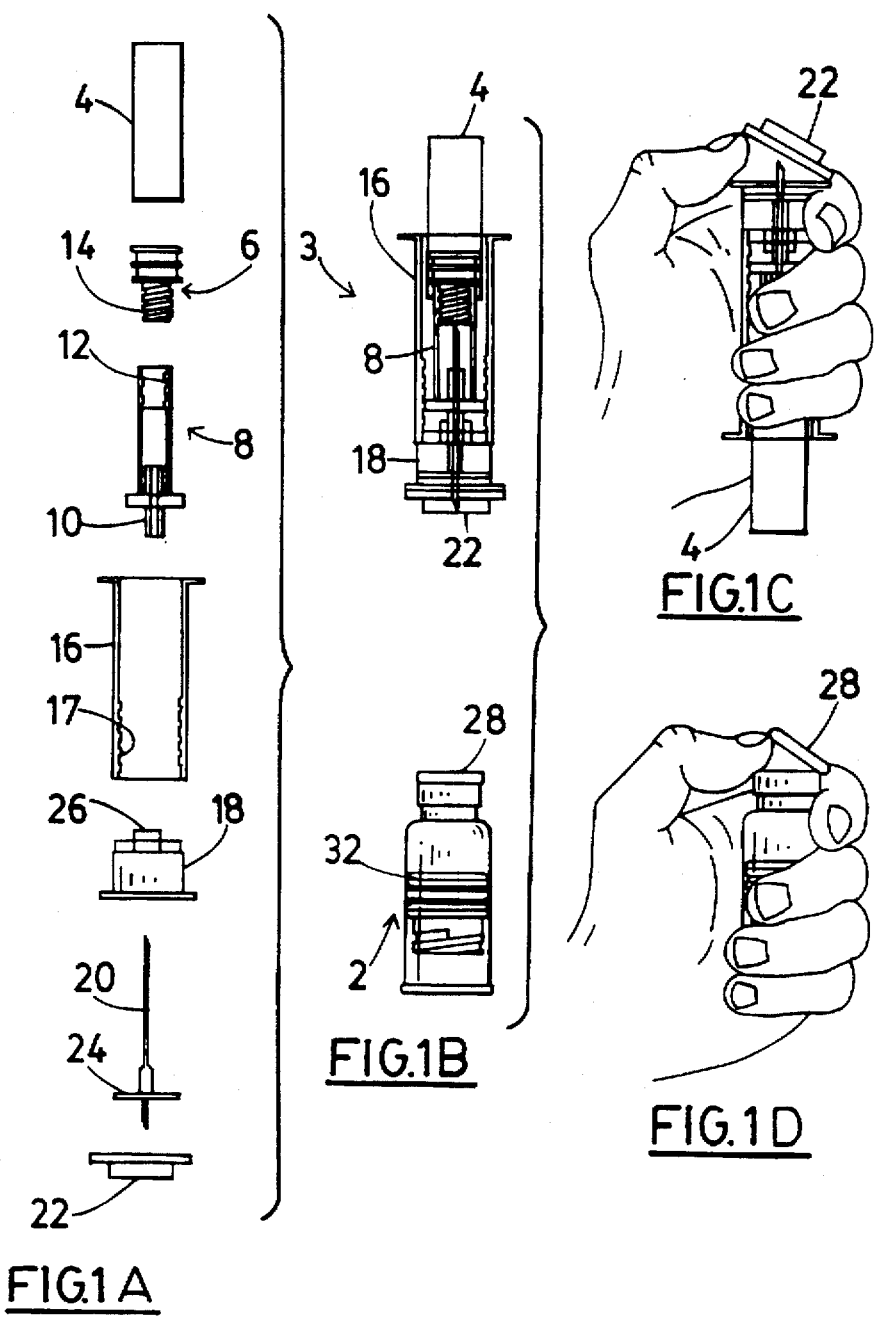

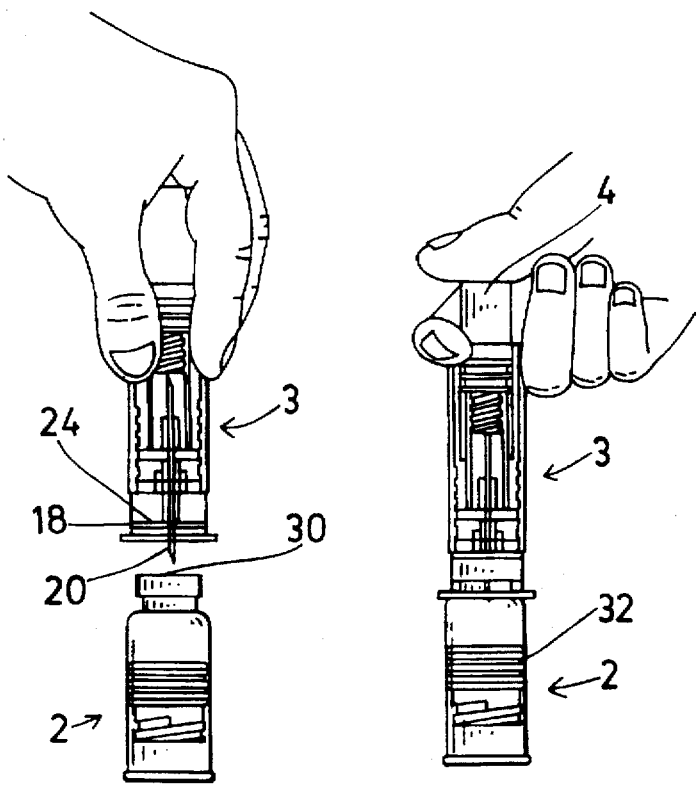
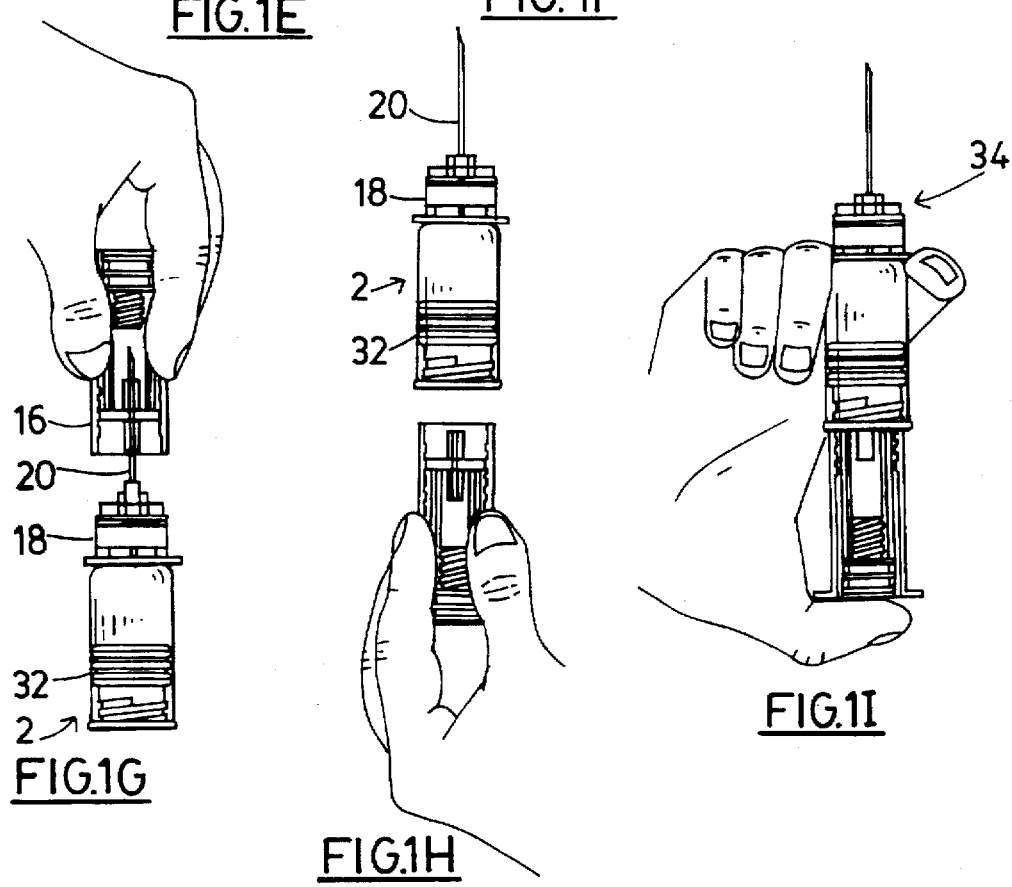
FIG.1E  FIG.1F
FIG.1G  FIG.1H  FIG.1I

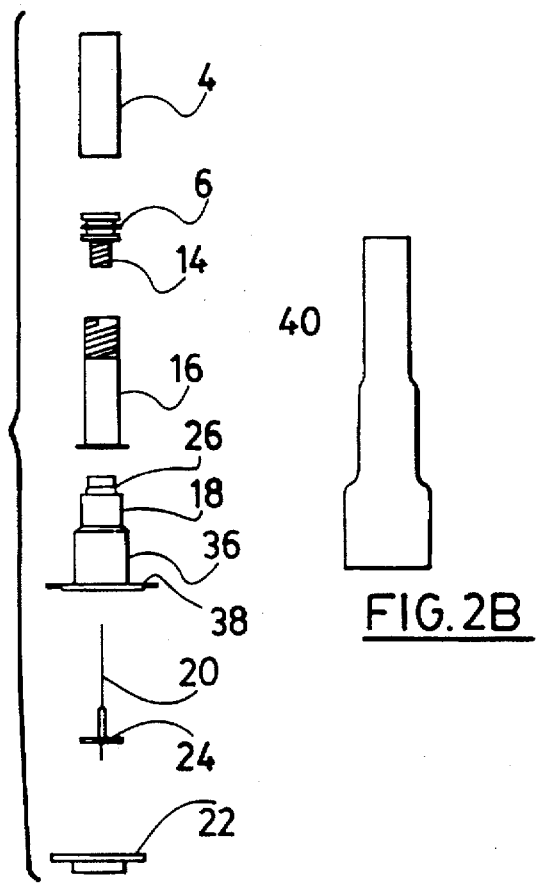
FIG. 2A
FIG. 2B
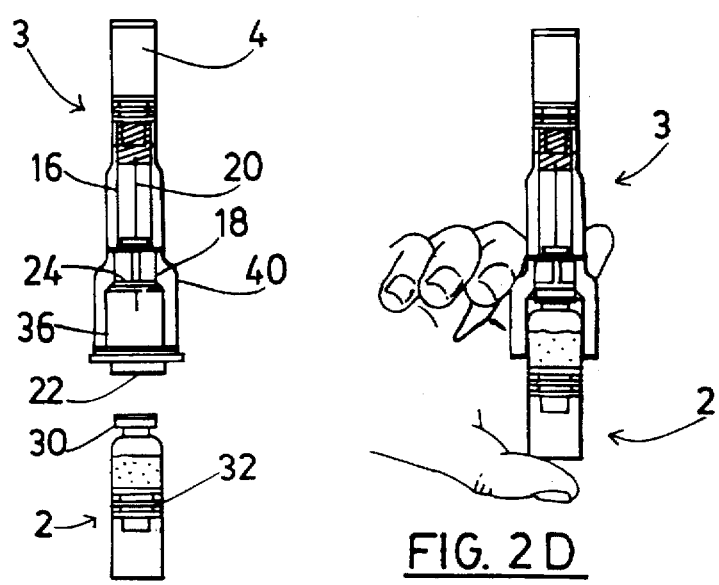
FIG. 2C
FIG. 2D

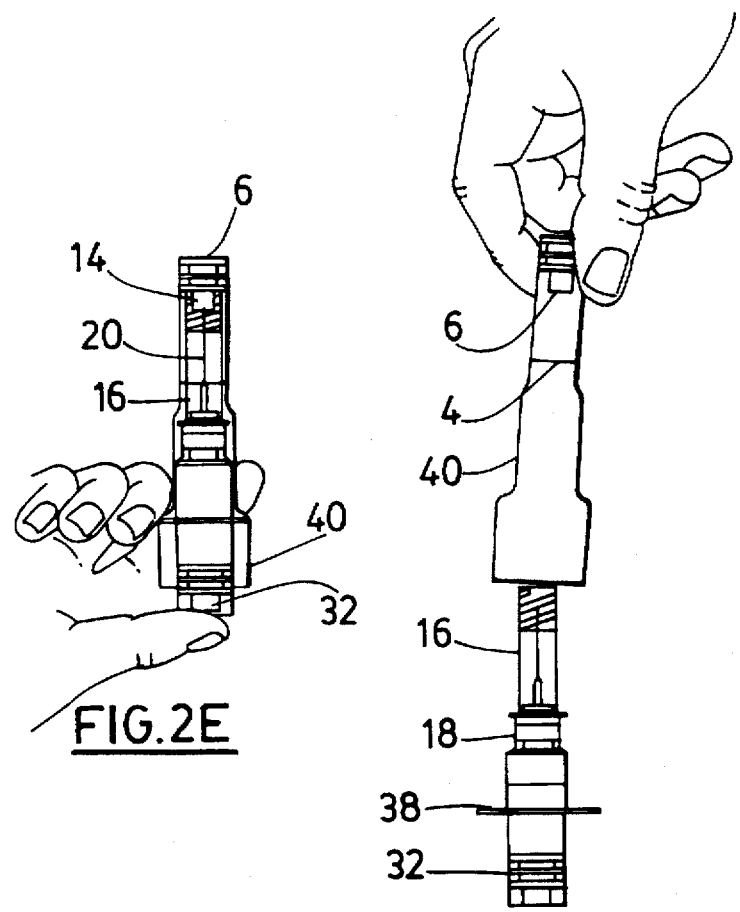
FIG. 2E
FIG. 2F
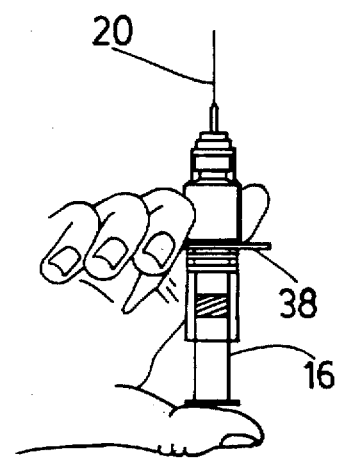
FIG. 2G

SYRINGE

REFERENCE TO RELATED APPLICATION

This application is a continuation-in-part of my application Ser. No. 07/791,399, filed Nov. 14, 1991, now U.S. Pat. No. 5,364,369.

TECHNICAL FIELD

This invention relates to prefilled syringe systems for the packaging of pharmaceutical preparations in dosage form, and more particularly to systems in which two components of a preparation, one of which is normally a diluent or solvent, must be stored separately and only admixed immediately prior to administration.

BACKGROUND ART

Our U.S. Pat. No. 5,137,511 describes several syringe systems for the packaging of two component pharmaceutical preparations, of which the system shown in FIGS. 11 and 12 is presently the most preferred. This system stores a solvent or diluent component in a specially formed capsule 14 which is described in detail in that patent.

Shell vials are however a well known and widely available packaging for pharmaceutical diluents. A shell vial differs from a conventional pharmaceutical or serum vial in that it has no neck. Instead the top of the vial is of the same diameter as the remainder of the cylindrical side wall of the vial, and is closed by a piston quite similar to that utilized by the present applicant to close the bottom of its bottomless vial as described in U.S. Pat. No. 5,137,511.

DISCLOSURE OF INVENTION

I have now found that the construction shown in this patent can be advantageously modified to utilize known shell vials in place of the capsule 14.

I have further found that in applications where shell vials are utilized, they may be replaced by bottomless vials such as are described in U.S. Pat. No. 5,137,511, which enables the advantages of such vials to be exploited in applications where shell vials might otherwise be utilized. A somewhat analogous substitution has previously been proposed in U.S. Pat. No. 3,845,763 (Cloyd), but the particular bottomless vial disclosed in that patent did not provide the manufacturing and other advantages of my bottomless vial as described in U.S. Pat. No. 5,137,511, and was not to the best of my knowledge pursued in any commercial product, the arrangement disclosed in U.S. Pat. No. 3,994,296 having been preferred commercially. My bottomless vial as described in U.S. Pat. No. 5,137,511 may also be advantageously substituted for the shell vial 4 in the device of the Cloyd '296 patent.

BRIEF DESCRIPTION OF DRAWINGS

Preferred embodiments of the invention are described with reference to the accompanying drawings, in which:

FIGS. 1A–1I are elevations illustrating successive stages in the assembly and preparation of use of a first embodiment of the invention, it being assumed for ease in illustration that most components other than those of rubber or metal are transparent; and FIGS. 2A–2G are elevations illustrating successive stages in the assembly and preparation for use of a second embodiment of the invention.

BEST MODES FOR CARRYING OUT THE INVENTION

FIG. 1A shows an exploded view of the components of a separately assembled and sterilized unit 3 (see FIG. 1B) for use in conjunction with a filled and capped vial 2 generally similar to that shown in FIG. 12 of U.S. Pat. No. 5,137,511. The unit 3 comprises a shell vial having a cylindrical body 4 closed at one end, and a piston 6 closing its other end to enclose a quantity of pharmaceutical diluent. A moulded plastic tubular adaptor component 8 has a tubular connector 10 at one end similar to the connector element 70 of U.S. Pat. No. 5,137,511, and an internal thread 12 within its other end forms a coupling engaged with an external thread on a extension 14 forming a coupling configuration on the piston 6. A tubular plunger 16 has an internal thread 17 which can provide a coupling to an integral extension or other coupling configuration on a piston 32 of the vial 2. This plunger and a cap 18 are similar to corresponding parts shown in U.S. Pat. No. 5,137,511. The unit further includes a cannula needle 20, and a protective cap 22 which closes the open end of the cap 18 to maintain sterility and provide protection of the needle during storage. The cap 22 is removed immediately before use (see FIG. 1C). The needle 20 is of the double ended type, and is located beneath the cap 18 by a flange 24. A connector 26 on the cap engages the connector 10 on the adaptor component 8 in the same way as the connector 27 engages the connector 70 in FIG. 12 of U.S. Pat. No. 5,137,511, so that one end of the needle 20 passes through the adaptor towards the piston extension 14, as seen in FIG. 1B.

After the cap 22 has been removed (FIG. 1C), as well as a flip-off protective cover 28 on the cap 30 of the vial 2, which protects a rubber closure of the vial held in place by the cap 30 (FIG. 1F), the unit 3 is pressed onto the vial 2 (FIG. 1F) so that the cap 18 is pressed over the cap 30 of the vial 2 so that the lower end of the needle 20 pierces a rubber closure of the vial 2. At the same time, the flange 24 is pressed upwardly within the cap 18 and causes the upper end of the needle 20 to penetrate a septum within the piston 6.

The shell vial 4 is then pressed downwardly (FIG. 1F) expelling its contents through the needle 20 into the vial 2. If necessary, the piston 32 within the vial 2 is positioned higher in the vial than normal so that it can be displaced downwardly to make room for the contents of vial 4 (see FIG. 1G).

At this point, the assembly 3, with the exception of the cap 18 and the needle 20, is pulled away from the vial 2 by gripping the plunger 16 leaving the cap and needle in place on the vial (FIG. 1G). The thread 17 of plunger 16 is then screwed onto the piston 32 of the vial 2 (FIG. 1H) to form a syringe 34 (FIG. 1I).

In the embodiment just described, the shell vial is dimensioned so as to fit within the tubular plunger. An alternative embodiment is shown in FIGS. 2A–G in which the shell vial 4 is dimensioned so that the tubular plunger 16 has an external diameter less than its internal diameter. The same reference numerals are used to denote those components of this embodiment which are similar to those of the previous embodiment, and only the differences will be described. In this instance, the plunger 16 fulfils the functions of the adaptor 8, the screw threads on extensions of the pistons 6 and 32 being similar except that the thread 14 on piston 6 may be longer. The plunger 16 is a press fit on the connector 26 on the cap 18, which in this case is formed with a skirt 36 which fits over the top portion of the vial 2 and also provides a finger grip 38. The entire unit 3 (see FIG. 2C) is assembled into a tubular sleeve 40 (FIG. 2B) which together with the cap 22 maintains sterility of the unit during storage, and also facilitates preparation of the syringe. The vial 4 is a press fit within the upper end of the sleeve 40. After removal of the cap 22, the unit 3 is applied to the vial (FIG.

2D) as in the previous embodiment, and the sleeve 40 is pulled downwardly (FIG. 2E). As before, this forces the cap 18 onto the cap 30 of the vial, causing the needle 20 to pierce both the closure of the vial 2 and the piston 6 of the shell vial 4, and further downward movement of the sleeve 40 forces the contents of the shell vial into the vial 2. At this point the sleeve 40 is rotated to unscrew the piston 6 of the shell vial 4 from the plunger 16 (FIG. 2F) which is then transferred to the piston 32 to complete the syringe.

It should be understood that the sleeve 40 could be omitted, although it is a convenience for packaging and manipulating the syringe, in which case the vial 4 would be manipulated directly rather than through the sleeve 40.

Variations in the above embodiments are possible. For some applications of the syringe, it may be desired to replace the needle 20 by some other cannula arrangement when the syringe is used, in which case a single ended needle may be located in the assembly 3 so that it will be forced upwardly as the cap 18 is forced onto the vial 2 (the cap in this case will have an internal cannula to pierce the closure of the vial), but will be retained within the shell vial when the latter is removed during preparation of the syringe. If a double ended needle 30 is used, in combination with a cannula, venting of the vial 2 to permit escape of air displaced by the contents of the shell vial 4 becomes possible, in a manner similar to that shown in FIG. 16 of U.S. Pat. No. 5,137,511.

In one particularly advantageous modification, the shell vial 4 and its associated piston 6 is replaced by a "bottomless vial" similar to the vial 2 except that its piston are dimensioned to have a similar diameter and diluent capacity to the shell vial 4. Such a prefilled bottomless vial, when so used, is functionally equivalent to a shell vial, but provides the manufacturing advantages set forth in U.S. Pat. No. 5,137,511. The term "shell vial" in the appended claims is to be interpreted to include such bottomless vials as well as conventional shell vials.

I claim:

1. A prefilled syringe system for two component pharmaceuticals, the system having in combination initially separate first and second sub-assemblies, of which the first sub-assembly comprises an open-bottomed pharmaceutical vial containing a first component of a pharmaceutical and having a filling neck, a first annular cap, a penetrable closure retained in said neck by said first annular cap, the vial having an open bottom end, a first piston hermetically closing said open bottom end and having a downwardly facing coupling configuration within the vial, and the second sub-assembly comprises a shell vial containing a second component of a pharmaceutical in the form of a fluid, a second piston closing an open end of the shell vial, a tubular guide member concentric with the shell vial such that the shell vial is movable from an initial position relative to the tubular guide member to telescope the vial and the tubular member together, the tubular guide member having a coupling at one end configured for subsequent coupling to the coupling configuration of said first piston to form a syringe plunger, a second cap releasably connected to said tubular member, which cap is internally dimensioned to receive said first cap as a press fit, and double-ended cannula means located concentrically within said second cap and projectable by pressing said first cap into second cap to penetrate both said penetrable closure and said second piston to place said bottomless vial and said shell vial in fluid communication through said cannula means whereby fluid from the shell vial is transferred to the bottomless vial upon telescoping said shell vial relative to said tubular guide member.

2. A syringe system according to claim 1, wherein the shell vial is of a diameter to telescope into said plunger, the second piston includes a coupling configuration facing the open end of the shell vial, and adaptor means is provided in said second subassembly extending between said second cap and the coupling configuration on said second piston to maintain the position of the latter during telescoping of the shell vial relative to the plunger.

3. A syringe system according to claim 1, characterized in that the shell vial is of a diameter to telescope around an exterior surface of said plunger, the second piston includes a coupling configuration facing the end of the shell vial, and said means on the plunger for coupling to the coupling configuration of the first piston is initially coupled to the coupling configuration on the second piston.

4. A syringe according to claim 3, including a tubular housing within which the components of the second subassembly are assembled, the shell vial being a press fit within the tubular housing.

5. A syringe system according to claim 1, wherein the cannula means is a double ended needle, and the needle has a radially extending flange to control its longitudinal position received within the second cap.

* * * * *